United States Patent
Malhotra et al.

(10) Patent No.: US 10,098,860 B2
(45) Date of Patent: Oct. 16, 2018

(54) BEZAFIBRATE FOR THE TREATMENT OF CANCER

(71) Applicant: Cipla Limited, Mumbai (IN)

(72) Inventors: Geena Malhotra, Mumbai (IN); Kalpana Joshi, Maharashtra (IN); Jeevan Ghosalkar, Thane (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 15/653,814

(22) Filed: Jul. 19, 2017

(65) Prior Publication Data

US 2018/0021276 A1  Jan. 25, 2018

(30) Foreign Application Priority Data

Jul. 20, 2016 (IN) .............................. 201621024898

(51) Int. Cl.
| | |
|---|---|
| *A61K 31/192* | (2006.01) |
| *A61K 31/404* | (2006.01) |
| *A61K 45/06* | (2006.01) |
| *A61K 9/00* | (2006.01) |

(52) U.S. Cl.
CPC .......... *A61K 31/192* (2013.01); *A61K 9/0053* (2013.01); *A61K 31/404* (2013.01); *A61K 45/06* (2013.01)

(58) Field of Classification Search
CPC .. A61K 31/192; A61K 9/0053; A61K 31/404; A61K 45/06
See application file for complete search history.

(56) References Cited

U.S. PATENT DOCUMENTS

| | | | |
|---|---|---|---|
| 5,304,575 A * | 4/1994 | Beck ...................... | A61K 31/19 514/563 |
| 2005/0004225 A1* | 1/2005 | Balendiran ............ | A61K 31/19 514/571 |

* cited by examiner

*Primary Examiner* — Sahar Javanmard
(74) *Attorney, Agent, or Firm* — Meunier Carlin & Curfman LLC

(57) ABSTRACT

Methods of treating renal cancer, including renal cell carcinoma, using bezafibrate are disclosed herein. Bezafibrate can be administered as a monotherapy or as part of a comprehensive treatment program, which can also include administration with other anti-cancer drugs, surgical treatments or exposure to ionizing radiation.

15 Claims, 5 Drawing Sheets

BEZAFIBRATE FOR THE TREATMENT OF CANCER

CROSS REFERENCE TO RELATED APPLICATION

This application claims the benefit of Indian Application 201621024898, filed on Jul. 20, 2016, the contents of which are incorporated herein in its entirety.

FIELD OF THE INVENTION

The invention is directed to the treatment of cancer, especially renal cell carcinoma, using bezafibrate, optionally in combination with one or more additional cancer therapeutics.

BACKGROUND

Renal cell carcinoma (RCC, also known as hypernephroma) is a kidney cancer that originates in the lining of the proximal convoluted tubule, the very small tubes in the kidney that transport GF (glomerular filtrate) from the glomerulus to the descending limb of the nephron. RCC is the most common type of kidney cancer in adults, responsible for approximately 80% of cases. It is also known to be the most lethal of all the genitourinary tumors. Initial treatment is most commonly a radical or partial nephrectomy and remains the mainstay of curative treatment. Where the tumor is confined to the renal parenchyma, the five year survival rate is 60-70%, but this is lowered considerably once metastases have spread. It is relatively resistant to radiation therapy and chemotherapy, although some cases respond to immunotherapy.

Renal-cell carcinoma affects approximately 150,000 people worldwide each year, causing close to 78,000 deaths annually, and its incidence seems to be increasing. RCC is not a single entity, but rather comprises the class of tumors of renal epithelial origin. Extensive histological and molecular evaluation has resulted in the development of a consensus classification of different RCC subtypes: (i) conventional (clear-cell) renal cell carcinoma; (ii) papillary renal cell-carcinoma; (iii) chromophobe renal carcinoma; (iv) oncocytoma; (v) collecting-duct carcinoma. Although most cases of RCC seem to occur sporadically, an inherited predisposition to renal cancer accounts for 1-4% of cases and could involve the same genes that cause sporadic renal cancer. Over the past two decades, studies of families with inherited RCC have laid the groundwork for the identification of seven hereditary renal cancer syndromes, and the predisposing genes for five of these have been identified. The surprisingly diverse nature of these genes implicates various mechanisms and biological pathways in RCC tumorigenesis.

RCC has been conventionally treated using surgery, radiation therapy, immunotherapy, and molecular-targeted therapy. Surgical resection remains the only known effective treatment for localized renal cell carcinoma, and it also is used for palliation in metastatic disease. Targeted therapy and immunomodulatory agents are considered standard of care in patients with metastatic disease.

Options for chemotherapy and endocrine-based approaches are limited, and no hormonal or chemotherapeutic regimen is accepted as a standard of care. Objective response rates with chemotherapy, either single-agent or combination, are usually lower than 15%. Therefore, various therapies have been evaluated.

The first agent, approved in late 2005, was sorafenib, after showing improvement in the second-line setting for progression-free survival (PFS) versus placebo. Shortly thereafter, sunitinib was approved following a large phase III trial that also demonstrated improvement in PFS versus interferon-α (INFα) in the first-line setting. The next agent approved was the mechanistic target of rapamycin (serine/threonine kinase) (mTOR) inhibitor, temsirolimus, which was evaluated as a first-line therapy against INFα in patients, most of whom had poor-risk disease. This trial demonstrated an improvement in overall survival (OS) in patients receiving temsirolimus. Combination of temsirolimus and INFα showed no advantages over the mTOR inhibitor alone. Meanwhile, everolimus was the second mTOR inhibitor approved after second-line therapy showed improvement in PFS versus placebo in a clinical trial. Pazopanib and axitinib are the two newer tyrosine kinase inhibitors and were recently approved for treatment of metastatic RCC. Patients taking pazopanib exhibited improved PFS versus those taking placebo both in the first-line setting and for cytokine-refractory disease. Axitinib was studied against sorafenib as a second-line agent and demonstrated improved PFS, while patient preference studies with pazopanib suggested improved tolerability. Yet another class of drug, an anti-PD-1 checkpoint inhibitor named as nivolumab, has been approved for intravenous administration that unleashes the body's immune system so that it can reject the kidney cancer, however, the drug may cause the body to develop an immune reaction against its own tissues thereby leading to wide range of side effects that can be severe or life-threatening. With multiple approved agents available, further research is yet to define the ideal timing, sequencing, and patient profile for a given particular agent.

Although, studies have demonstrated the general tolerability of targeted agents, at most occasions, most patients with RCC inevitably develop resistance to targeted agents after a median of 5-11 months of treatment. Combinations of targeted agents are being evaluated, but toxicity is problematic. Several strategies have been tested to manage the drug resistance including: Adjusting the dose of the drug, combination therapy or switching to an alternative agent. Moreover alternative pathways are currently under investigation particularly targeting of RAF (Rapidly Accelerated Fibrosarcoma), MEK (Mitogen-activated protein/extracellular signal-regulated kinase), and the PI3K (Phosphatidylinositol 3-kinase)/AKT (a serine/threonine kinase also known as protein kinase B [PKB]) pathway.

Based on the information available, even though there have been some advancements in the treatment of renal cell carcinomas, the associated complications like the disease stage, the response rate and the accompanying side effects potentially reduce the patient compliance and poses issues which severely affect the progression-free survival (PFS) and/or the overall survival (OS) which is the ultimate treatment goal for a given therapy.

There remains a need for improved and additional methods of treating renal cell carcinoma. There remains a need for additional small-molecule therapeutics for the treatment of renal cancer.

SUMMARY

According to one aspect of the present invention, there is provided a method of treating renal cell carcinoma (RCC) comprising administration of fibrate drugs such as bezafibrate.

According to another aspect of the present invention, there is provided a pharmaceutical composition comprising bezafibrate with one or more pharmaceutically acceptable excipients for the treatment of renal cell carcinoma (RCC).

According to another aspect of the present invention, there is provided a method of treating renal cell carcinoma (RCC) by administration of bezafibrate in combination with one or more additional cancer treatment regimens. The cancer treatment regimen can include administration of one or more additional therapeutic agents, exposure to ionizing radiation, and/or surgical interventions.

According to another aspect of the present invention, there is provided a use of bezafibrate in combination with one or more therapeutic agents either simultaneously, sequentially, or separately for the treatment of renal cell carcinoma (RCC). In some instances, the therapeutic agent can include one or more chemotherapeutic drugs.

According to another aspect of the present invention, there are provided pharmaceutical compositions and kits including bezafibrate and at least one other therapeutic agent.

The details of one or more embodiments are set forth in the descriptions below. Other features, objects, and advantages will be apparent from the description and from the claims.

DETAILED DESCRIPTION

Figure 1:
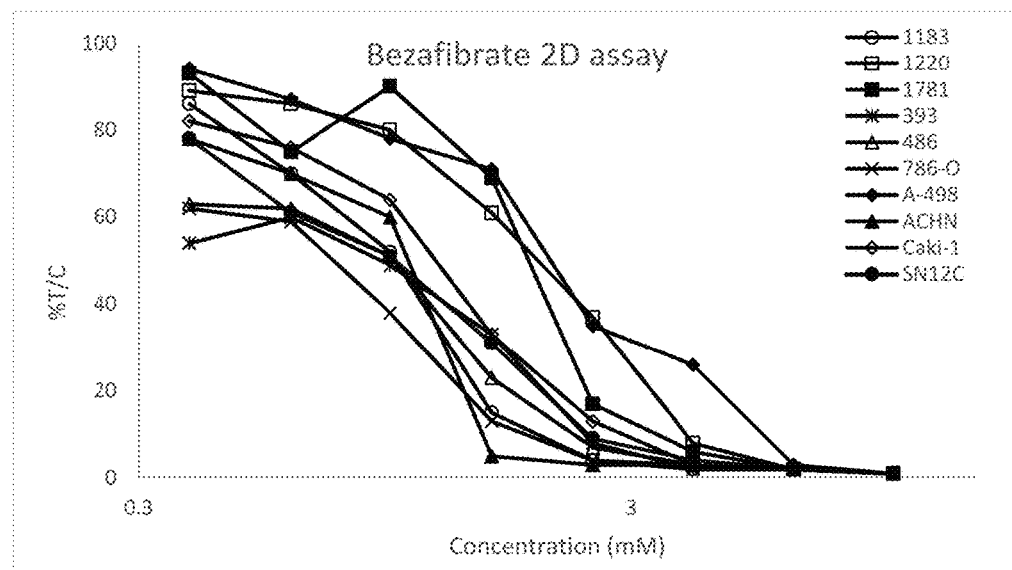
FIG. 1 depicts a concentration-effect curve exhibiting in-vitro efficacy of bezafibrate in human tumor cells in 2D model.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes ¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Renal cell carcinoma (RCC) is the most common type of kidney cancer. It accounts for more than 90% of malignant kidney tumours. Renal cell carcinoma consists of a heterogenous group of tumours with distinct genetic and metabolic defects and histopathologic and clinical features.

Bezafibrate is a fibric acid hypolipidemic agent chemically related to clofibrate. Because of its effectiveness in lowering VLDL cholesterol levels, it is used in the treatment of hyperlipidemias associated with high triglyceride levels. Like other fibrates, bezafibrate binds to the peroxisome proliferating activating receptor alpha (PPARα) triggering alterations in cholesterol levels. Bezafibrate is well absorbed following oral administration. Bezafibrate is chemically represented:

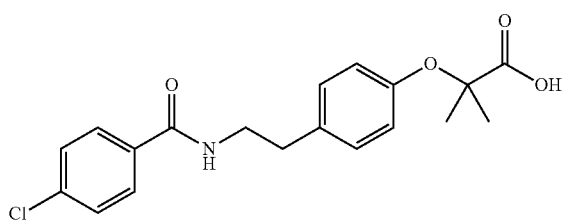 [SMILES: CC(C)(Oc1ccc(CCNC(=O)c2ccc(Cl)cc2)cc1)C(=O)O]

Bezafibrate is currently available under the trade name Bezalipx 200 mg tablets and Bezalip® SR 400 mg tablets. The recommended dosage is one Bezalip® 200 mg tablet thrice a day equivalent to 600 mg of bezafibrate or Bezalip® SR 400 mg sustained release tablet once daily equivalent to 400 mg of bezafibrate.

Bezafibrate is known to stimulate the expression of genes involved in fatty acid and lipoprotein metabolism thus resulting in a shift from hepatic fat synthesis to fat oxidation. It reduces triglycerides by 30-50% and moderately reduce (by 15-20%) low-density lipoprotein cholesterol (LDL-C). It also leads to a substantial reduction in serum triglycerides and an increase in high-density lipoprotein cholesterol levels. It is a synthetic pan peroxisome proliferator-activated receptor (PPAR) ligand agonist with increased specificity for PPARα as compared to PPARβ, PPARδ, and PPARγ.

Further, PPARγ is a nuclear receptor that regulates lipid homeostasis and is implicated in the pathology of numerous diseases, including cancer such as colon cancer, breast cancer, lung cancer and prostate cancer as well as inflammations.

The inventors of the present invention have found that bezafibrate optionally in combination with other anti-cancer agents exhibits a significant role in the inhibition of tumor growth, progression and metastasis of renal cell carcinoma.

As used herein, term "bezafibrate" is denoted in broad sense to include not only bezafibrate per se but also its pharmaceutically acceptable derivatives. Suitable pharmaceutically acceptable derivatives include pharmaceutically acceptable salts, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable polymorphs, pharmaceutically acceptable esters, pharmaceutically acceptable tautomers, pharmaceutically acceptable complexes etc.

Bezafibrate may be formulated as a pharmaceutically acceptable salt. Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, ptoluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

Bezafibrate may be formulated as pharmaceutically acceptable prodrug, for instance as an ester. Prodrugs can substantially increase the bioavailability of the compounds, permitting more effective oral therapy. In some embodiments, the prodrug is a $C_1$-$C_{10}$ alkyl ester of the 1-carboxylic acid, which may or may not be substituted. A preferred substituent is carbonyl-oxy and alkyloxy-carbonyloxy. Exemplary esters include methyl, ethyl, 2-morpholinylethyl, pivaloyloxy-methyl ester, 1-(isopropyloxy-carbonyloxy) ethyl ester, and 1-(acetyloxy)ethyl ester.

Bezafibrate can be administered according to various dosing regimens. For instance, bezafibrate can be administered once a day, twice a day, three times per day, or even more than three times a day. Bezafibrate can be administered such that the total daily dose is at least 50 mg, at least 100 mg, at least 250 mg, at least 500 mg, at least 750 mg, at least 1,000 mg, at least 1,250 mg, at least 1,500 mg, at least 1,750 mg, or at least 2,000 mg. In some instances, the total daily dose can be from 5-5,000 mg, 10-5,000 mg, 25-5,000 mg, 50-5,000 mg, 100-5,000 mg, 200-2,500 mg, 500-2,500 mg, 10-2,500 mg, 50-2,500 mg, 100-2,500 mg, 100-2,000 mg, 100-1,750 mg, 100-1,500 mg, 100-1,250 mg, 100-1,000 mg, 250-1,500 mg, 250-2,000 mg or 500-2,000 mg. In other embodiments, bezafibrate can be administered less than once daily, instance, once every two days, once every three days, once every five days, once every seven days, once every ten days, once every fourteen days, once every twenty-eight days or once every month.

In some instances, bezafibrate can be administered intermittently, for instance for a period of 1-10 days, followed by a period in which no bezafibrate is administered (e.g., 1-10 days), followed by another period e.g., 1-10 days, in which bezafibrate is administered. The on/off dosing schedule can be repeated as many times as necessary.

According to the present invention there is provided a pharmaceutical composition comprising bezafibrate with one or more pharmaceutically acceptable excipients for the treatment of renal cell carcinoma (RCC). Preferably, bezafibrate may be provided in the form of a pharmaceutical composition such as, but not limited to, solid unit dosage forms including tablets, capsules (filled with powders, pellets, beads, mini-tablets, pills, micro-pellets, small tablet units, multiple unit pellet systems (MUPS), disintegrating tablets, dispersible tablets, granules, microspheres and multiparticulates), sachets (filled with powders, pellets, beads, mini-tablets, pills, micro-pellets, small tablet units, MUPS, disintegrating tablets, dispersible tablets, granules, microspheres and multiparticulates), powders for reconstitution and sprinkles, however, other dosage forms such as controlled release formulations, lyophilized formulations, modified release formulations, delayed release formulations, extended release formulations, pulsatile release formulations, dual release formulations and the like may fall within the scope of the invention. Apart from this, it will be well acknowledged by person skilled in the art to have other forms of pharmaceutical compositions like liquid or semi-solid dosage form (liquids, suspensions, solutions, dispersions, ointments, creams, emulsions, microemulsions, sprays, spot-on), injection/parenteral preparations, topical, inhalations, buccal, nasal etc. and which may be envisaged under the ambit of the invention.

Depending on the pathological stage, patient's age and other physiological parameters, size of the tumor, and the extent of invasion, the pharmaceutical composition comprising bezafibrate may require specific dosage amounts and specific frequency of administrations. Preferably, on an average, the dose range that may be feasible for producing suitable anticancer effect may range from 25 mg to 3 gms depending on the above factors, and the route of administration adopted for administering the pharmaceutical composition. The dosing frequency that may be required for adherence to the therapy may be at least once, twice or thrice a day depending on the above mentioned factors and the route of administration adopted for administering the pharmaceutical composition.

It will further be well acknowledged by person skilled in the art that by specific treatment with bezafibrate, various physicochemical properties could be improved such as solubility, better absorption, bioavailability, increased shelf life, etc. and wherein such specific treatment refers to one or more of micronization and nanosizing techniques which may achieve one or more of the benefits aimed hereinabove, and may also assist in dose reduction. For instance, bezafibrate may be present in the form of nanoparticles which have an average particle size of less than 2,000 nm, less than 1,500 nm, less than 1,000 nm, less than 750 nm, less than 500 nm, or less than 250 nm.

Suitable pharmaceutically acceptable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, anti-microbial agents, antifoaming agents, emulsifiers, buffering agents, coloring agents, carriers, fillers, anti-adherents, solvents, taste-masking agents, preservatives, antioxidants, texture enhancers, surface stabilizers, channeling agents, coating agents or combinations thereof.

The present inventors have discovered the bezafibrate is surprisingly effective for the treatment of renal cell carcinoma. In certain embodiments, bezafibrate can be used to treat conventional (clear-cell) renal cell carcinoma, papillary renal cell-carcinoma, chromophobe renal carcinoma, oncocytoma, or collecting-duct carcinoma. Renal cell carcinoma can be classified in stages, according to the extent of disease progression. The TNM (tumor size/lymph node/metastasis) system includes the following stages of RCC:

Stage I: Tumor of a diameter of 7 cm (approx. 2¾ inches) or smaller, and limited to the kidney, with no lymph node involvement or metastases to distant organs.

Stage II: Tumor larger than 7.0 cm but still limited to the kidney, with no lymph node involvement or metastases to distant organs.

Stage III: Tumor of any size with involvement of a nearby lymph node but no metastases to distant organs. Tumor of this stage may be with or without spread to fatty tissue around the kidney, with or without spread into the large veins leading from the kidney to the heart; or Tumor with spread to fatty tissue around the kidney and/or spread into the large veins leading from the kidney to the heart, but without spread to any lymph nodes or other organs; or Tumor with spread to fatty tissue around the kidney and/or spread into the large veins leading from the kidney to the heart, but without spread to any lymph nodes or other organs.

Stage IV: Tumor that has spread directly through the fatty tissue and the fascia ligament-like tissue that surrounds the kidney; or involvement of more than one lymph node (near or distant from kidney); or distant metastases, such as in the lungs, bone, or brain.

Bezafibrate can be used to treat Stage I RCC, Stage II RCC, Stage III RCC, or Stage IV RCC. In some embodiments, bezafibrate can be administered in an amount effective to reduce tumor size, inhibit tumor growth, alleviate symptoms, delay progression, prolong survival, including, but not limited to disease free survival, prevent or delay RCC metastasis, reduce or eliminate preexisting RCC metastasis, and/or prevent recurrence of RCC. All of these effects fall within the general scope of treating RCC.

As used herein, the term "delay" refers to methods that reduce the probability of disease development/extent in a given time frame, when compared to otherwise similar methods that do not include the use of bezafibrate. Probabilities can be established using clinical trials, but can also be determined using in vitro assays when correlations have been established. In some embodiments, bezafibrate can inhibit renal cancer cell proliferation. For instance, at least about 10%, at least about 20%, at least about 30%, at least about 40%, at least about 50%, at least about 60%, at least about 70%, at least about 80%, at least about 90%, or 100% of cell proliferation is inhibited upon administration of a therapeutically effective amount of bezafibrate. In some embodiments, bezafibrate can inhibit renal cancer metastasis. For instance, at least about 10%, at least about 20%, at least about 30%, at least about 40%, at least about 50%, at least about 60%, at least about 70%, at least about 80%, at least about 90%, or 100% of metastasis is inhibited upon administration of a therapeutically effective amount of bezafibrate. Bezafibrate can also be used to reduce tumor volume. For instance, tumor volume can be reduced by at least about 10%, at least about 20%, at least about 30%, at least about 40%, at least about 50%, at least about 60%, at least about 70%, at least about 80%, or at least about 90% of tumor volume can be reduced upon administration of a therapeutically effective amount of bezafibrate.

According to the present invention, there is provided a method of alleviating or treating renal cell carcinoma (RCC) by administration of bezafibrate in combination with one or more anti-cancer drugs either simultaneously, sequentially, or separately. In certain embodiments, bezafibrate can be administered with:

(A) cytotoxic anti-neoplastic drugs such as nucleoside analogues, antifolates, antimetabolites, topoisomerase I inhibitor, anthracyclines, podophyllotoxins, taxanes, *vinca* alkaloids, alkylating agents, platinum compounds, proteasome inhibitors, nitrogen mustards & oestrogen analogue; and/or (B) targeted anti-neoplastic drugs such as monoclonal antibodies, tyrosine kinase inhibitors, mTOR inhibitors, retinoids, immunomodulatory agents, histone deacetylase inhibitors, other kinase inhibitors.

In some embodiments, bezafibrate may be administered (simultaneously, sequentially or separately) with one or more anti-cancer drugs. Such drugs include small molecule chemical agents and biological agents, including immunotherapies. Exemplary anti-cancer drugs include Abiraterone acetate, Methotrexate, Paclitaxel Albumin-stabilized Nanoparticle, Brentuximab Vedotin, Ado-Trastuzumab Emtansine, Doxorubicin Hydrochloride, Afatinib Dimaleate, Everolimus, Netupitant, Palonosetron Hydrochloride, Imiquimod, Aldesleukin, Alectinib, Alemtuzumab, Melphalan Hydrochloride, Melphalan, Pemetrexed Disodium, Chlorambucil, Aminolevulinic acid, Anastrozole, Aprepitant, Pamidronate Disodium, Exemestane, Nelarabine, Arsenic Trioxide, Ofatumumab, Asparaginase *Erwinia chrysanthemi*, Atezolizumab, Bevacizumab, Axitinib, Azacitidine, Carmustine, Belinostat, Bendamustine hydrochloride, Bevacizumab, Bexarotene, Tositumomab, Bicalutamide, Bleomycin, Blinatumomab, Blinatumomab, Bortezomib, Bosutinib, Busulfan, Cabazitaxel, Cabozantinib, Alemtuzumab, Irinotecan hydrochloride, Capecitabine, Fluorouracil, Carboplatin, Carfilzomib, Bicalutamide, Lomustine, Ceritinib, Daunorubicin Hydrochloride, Cetuximab, Chlorambucil, Cyclophosphamide, Clofarabine, Cobimetinib, Dactinomycin, Cobimetinib, Crizotinib, Ifosfamide, Ramucirumab, Cytarabine, Dabrafenib, Dacarbazine, Decitabine, Daratumumab, Dasatinib, Daunorubicin hydrochloride, Decitabine, Efibrotide Sodium, Defibrotide sodium, Degarelix, Denileukin Diftitox, Denosumab, Dexamethasone, Dexrazoxane hydrochloride, Dinutuximab, Docetaxel, Doxorubicin Hydrochloride, Dacarbazine, Rasburicase, Epirubicin hydrochloride, Elotuzumab, Oxaliplatin, Eltrombopag olamine, Aprepitant, Elotuzumab, Enzalutamide, Epirubicin Hydrochloride, Cetuximab, Eribulin Mesylate, Vismodegib, Erlotinib hydrochloride, Etoposide, Raloxifene hydrochloride, Melphalan hydrochloride, Toremifene, Panobinostat, Fulvestrant, Letrozole, Filgrastim, Fludarabine phosphate, Flutamide, Methotrexate, Pralatrexate, Recombinant HPV Quadrivalent Vaccine, Recombinant HPV Nonavalent vaccine, Obinutuzumab, Gefitinib, Gemcitabine hydrochloride, Gemtuzumab Ozogamicin, Afatinib Dimaleate, Imatinib Mesylate, Glucarpidase, Goserelin acetate, Eribulin mesylate, Trastuzumab, Topotecan hydrochloride, Palbociclib, Ibritumomab tiuxetan, Ibrutinib, Ponatinib hydrochloride, Idarubicin hydrochloride, Idelalisib, Imiquimod, Axitinib, Recombinant Interferon Alfa-2b, Tositumomab, Ipilimumab, Gefitinib, Romidepsin, Ixabepilone, Ixazomib Citrate, Ruxolitinib phosphate, Cabazitaxel, Ado-Trastuzumab Emtansine, Palifermin, Pembrolizumab, Lanreotide Acetate, Lapatinib ditosylate, Lenalidomide Lenvatinib mesylate, Leuprolide acetate, Olaparib, Vincristine Sulfate, Procarbazine hydrochloride, Mechlorethamine hydrochloride, Megestrol Acetate, Trametinib, Mercaptopurine, Temozolomide, Mitoxantrone hydrochloride, Plerixafor, Busulfan, Azacitidine, Gemtuzumab Ozogamicin, Vinorelbine tartrate, Necitumumab, Nelarabine, Sorafenib tosylate, Nilotinib, Ixazomib citrate, Nivolumab, Romiplostim, Obinutuzumab, Ofatumumab, Olaparib, Omacetaxine mepesuccinate, Pegaspargase, Ondansetron hydrochloride, Osimertinib, Panitumumab, Panobinostat, Peginterferon Alfa-2b, Pembrolizumab, Pertuzumab, Plerixafor, Pomalidomide, Ponatinib hydrochloride, Necitumumab, Pralatrexate, Procarbazine hydrochloride, Aldesleukin, Denosumab, Ramucirumab, Rasburicase, Regorafenib, Lenalidomide, Rituximab, Rolapitant hydrochloride, Romidepsin, Ruxolitinib phosphate, Siltuximab, Dasatinib, Sunitinib malate, Thalidomide, Dabrafenib, Osimertinib, Talimogene, Atezolizumab, Temsirolimus, Thalidomide, Dexrazoxane hydrochloride, Trabectedin, Trametinib, Trastuzumab, Lapatinib ditosylate, Dinutuximab, Vandetanib, Rolapitant hydrochloride, Bortezomib, Venetoclax, Crizotinib, Enzalutamide, Ipilimumab, Trabectedin, Ziv-Aflibercept, Idelalisib, and Ceritinib. Preferred agents for use in combination with bezafibrate include bevacizumab, axitinib, sorafenib, sunitinib, everolimus, temsirolimus, pazopanib, and lenvatinib. An especially preferred agent is sunitinib Bezafibrate can be administered with one or more chemotherapeutic agents either simultaneously, sequentially, or separately. In certain cases, bezafibrate can be administered for a period of at least 1 week, at least 2 weeks, at least 4 week, at least 6 weeks, at least 8 week, or at least 10 weeks, prior to commencing treatment with additional agents. In some instances, bezafibrate and the other agent can be administered intermittently, for instance a period of bezafibrate administration, followed by a period in which the other agent to administered, followed by another period of bezafibrate administration. The cycle can be repeated as many times as necessary.

In certain cases, the combination of bezafibrate and additional agent will exhibit a greater than additive effect (i.e., a synergistic effect). In other instance, the use of bezafibrate permits a reduced amount of the other agent to be administered, without a corresponding decrease in therapeutic efficiency.

In cases of combination therapy, it is possible that a unitary dosage form comprising both bezafibrate and one or more additional anti-cancer drugs may be employed. In some instances, the combinations may be provided in form of kit including a unitary dosage form containing both bezafibrate and at least one other therapeutic agent, or a kit having bezafibrate and an additional agent in separate dosage forms. In some embodiments, bezafibrate is present in an oral or parenteral composition and the additional anti-cancer drug therapy may be provided in an oral or parenteral composition. In one embodiment, the kit preparation may be provided in an all oral dosage form presentation wherein both the bezafibrate and the additional anti-cancer drug are presented in an oral dosage form. In another embodiment, the kit preparation may be provided as an oral plus parenteral dosage form presentation wherein bezafibrate is presented in an oral form and the additional anti-cancer drug is presented in a parenteral form. Alternatively, the kit preparation may be provided wherein bezafibrate is presented in a parenteral form and the additional anti-cancer drug is presented in an oral dosage form.

In some instances, bezafibrate can be used in combination with ionizing radiation and/or surgical interventions for the treatment of RCC. Bezafibrate can be administered before, during, or after treatment with ionizing radiation or surgical intervention. In certain cases, bezafibrate can be administered for a period of at least 1 week, at least 2 weeks, at least 4 week, at least 6 weeks, at least 8 week, or at least 10 weeks, prior to commencing treatment with ionizing radiation or surgery. Exemplary forms of radiation include x-rays, gamma rays, electron beams and proton beams. It has been found that administration of bezafibrate permits a reduction in the total exposure of the patient to ionizing radiation, without a corresponding reduction in therapeutic efficiency. In certain instances, bezafibrate can be administered both prior and subsequent to ionizing radiation and/or surgical interventions. For instance, bezafibrate can be administered for a period of at least 1 week, at least 2 weeks, at least 4 week, at least 6 weeks, at least 8 week, or at least 10 weeks, following treatment with ionizing radiation or surgery.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results.

These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: In Vitro 2D Assay

Cell lines RXF 1183L, RXF 1220L, RXF 1781L, RXF 393L and RXF 486L were established at Oncotest from the corresponding human patient-derived xenograft. The cell lines 786-O, A-498, Caki-1 and SN12C were purchased from NCI (National Cancer Institute, Bethesda, Md., USA). ACHN was purchased from ECACC (European Collection of Cell Cultures, Salisbury, UK). Authenticity of cell lines was confirmed at the DSMZ by STR (short tandem repeat) analysis, a PCR based DNA-fingerprinting methodology.

Cell lines were routinely passaged once or twice weekly and maintained in culture for up to 20 passages. All cells were grown at 37° C. in a humidified atmosphere with 5% $CO_2$ in RPMI 1640 medium (25 mM HEPES, with L-glutamine, #FG1385, Biochrom, Berlin, Germany) supplemented with 10% (v/v) fetal calf serum (Sigma, Taufkirchen, Germany) and 0.1 mg/mL gentamicin (Life Technologies, Karlsruhe, Germany).

Bezafibrate was dissolved at a concentration of 100 mM in 100% Methanol and next 1:5 diluted with cell culture media (20 mM, 20% Methanol). Starting with this solution, serial dilutions (1:1.6) were prepared with cell culture medium. Next, 150 µL of the serial dilutions were transferred to the assay plates upon removing the cell culture media of each well (complete change of medium on assay plates). Thus the final test concentrations were 10,240, 6,400, 4,000, 2,500, 1,563, 977, 610, and 381 µM. The maximum methanol concentrations were 6% and 10%. No precipitation was observed.

Cells were harvested from exponential phase cultures, counted and plated in 96-well flat-bottom microtiter plates at a cell density of 4,000-12,000 cells/well depending on the cell line's growth rate. After a 24 hour recovery period to allow the cells to resume exponential growth, test compounds were added. Compounds were applied at 8 to 10 concentrations in duplicate and treatment continued for 96 hour. After 96 hour treatment of cells, 20 µL/well CellTiter-Blue® reagent was added. Following an incubation period of up to four hours, fluorescence (FU) was measured by using the Enspire Multimode Plate Reader (excitation $\lambda$=531 nm, emission $\lambda$=615 nm).

For calculations, the mean values of duplicate/quadruplicate (untreated control) data were used. Sigmoidal concentration-response curves were fitted to the data points (T/C values) obtained for each cell line using 4 parameter non-linear curve fit.

Bezafibrate was tested in two independent runs by using different ranges of concentrations. In the first run bezafibrate was tested in the range from 93 to 4,000 µM, in the second run from 381 to 10,240 µM. In both runs bezafibrate displayed a concentration-dependent activity with sigmoidal concentration-effect curves in all cell lines tested with a geometric mean absolute $IC_{50}$ value of 1,776 µM and 1,222 µM, respectively. In the first run individual IC50 values were in the range from 1,069 µM (ACHN) to 3,412 µM (1220L) and in the second run between 795 µM (786-O) and 2,122 µM (A-498) (FIG. 1).

Overall, concentration dependent anti-cancer activity with IC50 values in the low mM range was detected for bezafibrate.

TABLE 1

Relative and Absolute $IC_{50}$ values for Bezafibrate across the human tumor cell models for RCC in in vitro 2D model.

| Cell line | Absolute $IC_{50}$ µM | Relative $IC_{50}$ µM |
|---|---|---|
| 1183 | 960 | 1056 |
| 1220 | 1930 | 2106 |
| 1781 | 1862 | 1946 |
| 393 | 1037 | 1642 |
| 486 | 987 | 1328 |
| 786-O | 795 | 1073 |
| A-498 | 2122 | 2277 |
| ACHN | 1051 | 1127 |
| Caki-1 | 1229 | 1398 |
| SN12C | 966 | 1206 |
| Geometric mean | 1222 | 1559 |

Example 2: In Vitro 3D Assay

Cell lines were routinely passaged one or twice weekly. All cells were grown at 37° C. in a humidified atmosphere with 5% $CO_2$ in RPMI 1640 medium (Biochrom) supplemented with 10% (v/v) fetal calf serum and 0.1 mg/mL gentamicin. The percentage of viable cells was determined in a Neubauer-hemocytometer using trypan blue exclusion.

Tumor xenografts (patient-derived, as well as cell line-derived xenografts) were passaged as subcutaneous xenografts in NMRI nu/nu mice. At a tumor volume of 400-1,000 $mm^3$ tumor-bearing mice were sacrificed and tumors were collected under sterile conditions without delay according to the relevant Oncotest SOPs and the relevant animal welfare guidelines published by the FELASA and the GV-SOLAS. Tumors were mechanically disaggregated and subsequently incubated with an enzyme cocktail consisting of collagenase type IV (41 U/mL), DNase I (125 U/mL), hyaluronidase type III (100 U/mL), and dispase II (1.0 U/mL) in RPMI 1640 medium (Life Technologies) at 37° C. for 60-120 minutes. Cells were passed through sieves of 100 µm and 40 µm mesh size (Cell Strainer, BD Falcon™), and washed with RPMI 1640 medium. The percentage of viable cells was determined in a Neubauer-hemocytometer using trypan blue exclusion. Aliquots of the cells were frozen down, and stored in liquid nitrogen. On each day of an experiment, a frozen aliquot of tumor cells was thawed and used for preparation of assay plates.

The clonogenic assay was carried out in a 96 well plate format using ultra low attachment plates. For each test, cells were prepared as described above and assay plates were prepared as follows: each test well contained a layer of semi-solid medium with tumor cells (50 μL), and a second layer of medium supernatant with or without test compound (100 μL). The cell layer consisted of $2.5 \cdot 10^3$ to $1 \cdot 10^4$ tumor cells per well, which were seeded in 50 μL/well cell culture medium (IMDM, supplemented with 20% (v/v) fetal calf serum, 0.01% (w/v) gentamicin, and 0.4% (w/v) agar). After 24 hours the test compounds were added after serial dilution in cell culture medium, and left on the cells for the duration of the experiment (continuous exposure, 100 μl drug overlay). Every plate included six untreated control wells and drug-treated groups in duplicate at 9 concentrations. Cultures were incubated at 37° C. and 7.5% $CO_2$ in a humidified atmosphere for 8 to 13 days and monitored closely for colony growth using an inverted microscope. Within this period, ex vivo tumor growth led to the formation of colonies with a diameter of >50 μm. At the time of maximum colony formation, counts were performed with an automatic image analysis system (CellInsight NXT, Thermo Scientific). 48 hours prior to evaluation, vital colonies were stained with a sterile aqueous solution of 2-(4-iodophenyl)-3-(4-nitrophenyl)-5-phenyltetrazolium chloride (1 mg/ml, 100 μl/well).

Figure 2:
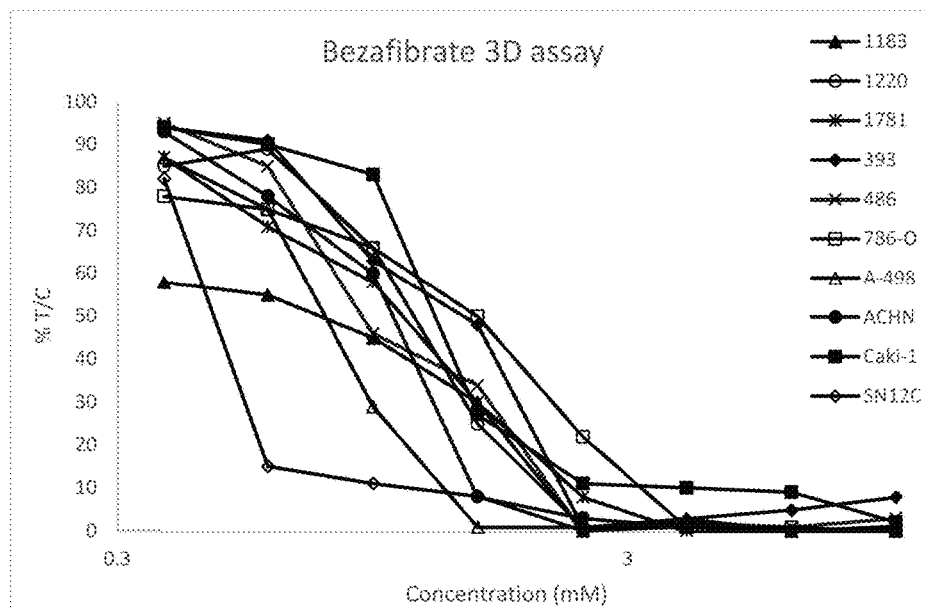
FIG. 2 depicts a concentration-effect curve in-vitro exhibiting efficacy of bezafibrate in human tumor 3D model.

Bezafibrate inhibited colony formation in a concentration-dependent manner with a mean relative $IC_{50}$ value of 985 μM (mean absolute $IC_{50}$ value=945 μM). Bottom plateaus of the concentration-effect curves of responding tumor models were in the range from 0 to 18%, indicating clear inhibition of tumor colony growth in the selected test range. Based on relative $IC_{50}$ values, above average activity was observed for bezafibrate against SN12C cells ($IC_{50}$=463 μM) (FIG. 2).

TABLE 2

Relative and Absolute $IC_{50}$ values for Bezafibrate across the human tumor cell models for RCC in in vitro 3D model.

| Cell line | Absolute $IC_{50}$ μM | Relative $IC_{50}$ μM |
| --- | --- | --- |
| 1183 | 609 | 712 |
| 1220 | 1162 | 1232 |
| 1781 | 1029 | 1104 |
| 393 | 1270 | 1276 |
| 486 | 993 | 962 |
| 786-O | 1336 | 1474 |
| A-498 | 764 | 773 |
| ACHN | 1013 | 1057 |
| Caki-1 | 1287 | 1290 |
| SN12C | 463 | 463 |
| Geometric mean | 945 | 985 |

Example 3: In Vitro 3D Combination Assay

The objective of the study was to assess anti-tumor efficacy of bezafibrate in combination with sunitinib in a 5×5 matrix combination format against tumor cell lines of renal cancer using a clonogenic assay with image analysis as read-out. The Bliss independence methodology was used for data analysis, in order to identify possible synergistic effects.

The clonogenic assay was carried out in a 96 well plate format using ultra low attachment plates. The assay plates were prepared as follows: each test well contained a layer of semi-solid medium with tumor cells (50 μl), and a second layer of medium supernatant with or without test compounds (100 μl). The cell layer consisted of $3 \times 10^3$ to $1 \times 10^4$ tumor cells per well, which were seeded in 50 μl/well cell culture medium (IMDM, supplemented with 20% (v/v) fetal calf serum, 0.01% (w/v) gentamicin, and 0.4% (w/v) agar). The soft-agar layer was immediately covered with 90 μl of the same culture medium without agar. After 24 hours the test compounds were added after serial dilution in IMDM and transfer in cell culture medium, and left on the cells for the duration of the experiment (continuous exposure, 100 μL total drug overlay). Every plate included six untreated control wells and drug-treated groups. Cultures were incubated at 37° C. and 7.5% $CO_2$ in a humidified atmosphere for 8 or 13 days and monitored closely for colony growth using an inverted microscope. Within this period, ex vivo tumor growth led to the formation of colonies with a diameter of >50 μm. At the time of maximum colony formation, counts were performed with an automatic image analysis system (CellInsight NXT, Thermo Scientific). 48 hours prior to evaluation, vital colonies were stained with a sterile aqueous solution of 2-(4-iodophenyl)-3-(4-nitrophenyl)-5-phenyltetrazolium chloride (1 mg/ml, 100 μl/well).

Figure 3:
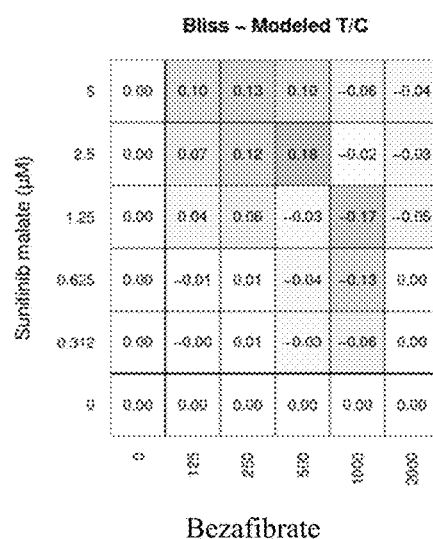
FIG. 3 includes a depiction of the anti-tumor efficacy of Bezafibrate in combination with Sunitinib against cell line RXF1183L. Bliss index indicates the difference of Bliss neutral and modeled T/C for each pair of conditions. Where positive values (Bliss Index ≥0.15) indicate synergism, negative values (Bliss Index ≤−0.15) indicate antagonism, and zero is the neutral value.
Figure 4:
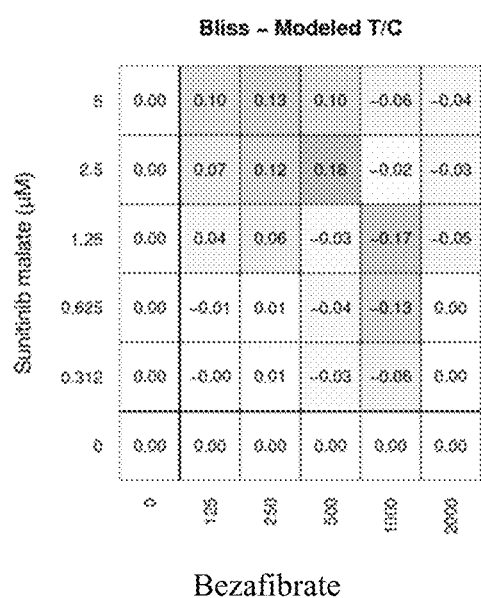
FIG. 4 includes a depiction of the anti-tumor efficacy of Bezafibrate in combination with Sunitinib against cell line RXFSN12C. Bliss index indicates the difference of Bliss neutral and modeled T/C for each pair of conditions. Where positive values (Bliss Index ≥0.15) indicate synergism, negative values (Bliss Index <−0.15) indicate antagonism, and zero is the neutral value.
Figure 5:
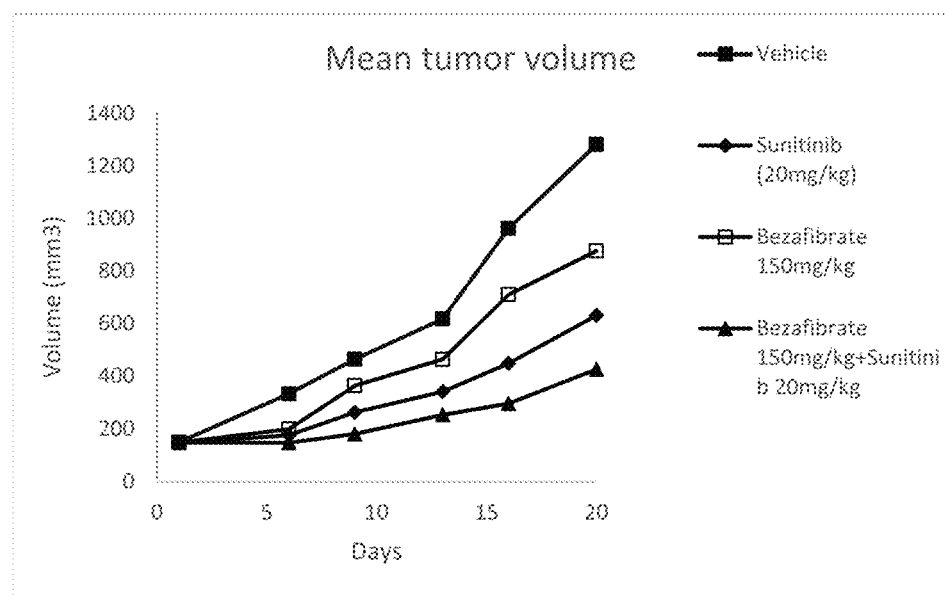
FIG. 5 includes a graphical representation of mean tumor volume across the animal group populations G1 (vehicle), G2 (sunitinib), G3 (bezafibrate), and G4 (bezafibrate and sunitinib).
Figure 6:
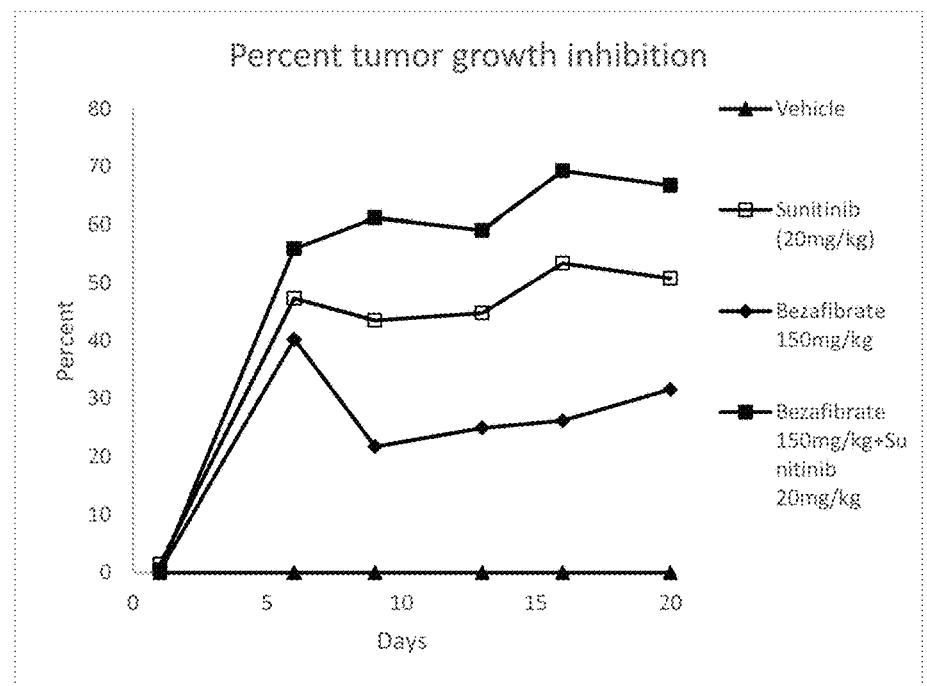
FIG. 6 includes a graphical representation of mean tumor growth inhibition (in percentage value) across the animal group populations G1 (vehicle), G2 (sunitinib), G3 (bezafibrate), and G4 (bezafibrate and sunitinib).
Figure 7:
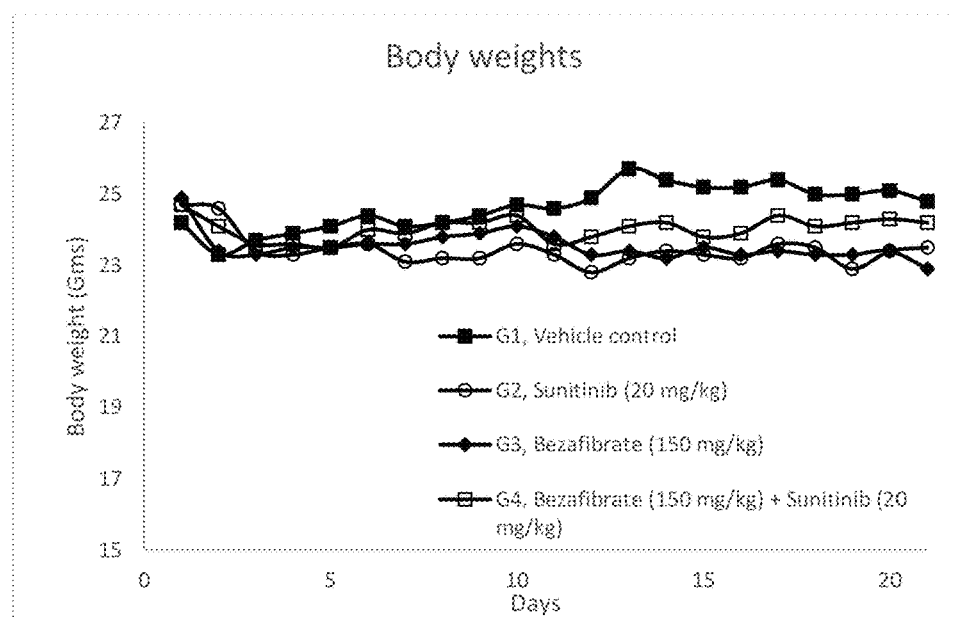
FIG. 7 includes a graphical representation depicting change in body weights across the animal group population G1 (vehicle), G2 (sunitinib), G3 (bezafibrate), and G4 (bezafibrate and sunitinib).

Bezafibrate was tested alone and in combination with sunitinib in order to investigate the ability to inhibit anchorage-independent growth and ex vivo colony formation of tumor cells in semi-solid medium. Bezafibrate was tested against RXF 1183L and RXF SN12C at concentrations ranging from 125 μM to 2000 μM, Sunitinib was tested at concentrations ranging from 0.3125 μM to 5 μM against all cell lines. Results are depicted in FIGS. 3 and 4.

Example 4: In Vivo Animal Efficacy Study

Healthy 10 female athymic nude mice were recruited for the donor cell inoculation. Animals were subcutaneously injected at flank region with 10 million A498 cells suspended in 200 μl of media and matrigel. Animals were monitored for solid tumor growth. Once the tumor reached ~500 mm³, donor animals were humanely sacrificed and tumors were collected under aseptic condition. Tumors were fragmented in to ~30 mg size.

After one week of acclimatization, female athymic nude mice were subcutaneously implanted with ~30 mg tumor fragments using the device trocar. Animals were observed for tumor growth for next three weeks. Tumor bearing animals were selected from the experimental animals and grouped on basis of tumor size, into four groups containing 7 animals in each group as mentioned below.

| Group | Treatment | Dose, Route & Regimen | No. of Animals |
| --- | --- | --- | --- |
| G1 | Vehicle, 0.5% CMC | 10 mL/kg, p.o. q.d. × 21 | 7 |
| G2 | Sunitinib | 20 mg/kg, p.o. q.d. × 21 | 7 |
| G3 | Bezafibrate | 150 mg/kg, p.o. q.d. × 21 | 7 |
| G4 | Bezafibrate + Sunitinib | 150 mg/kg, p.o. q.d. × 21 + 20 mg/kg, p.o. q.d. × 21 | 7 |

The tumor sizes were measured weekly twice from the date of tumor appearance till the end of the experiment. Tumor size was measured by digital vernier caliper (MITU-TOYO) by measuring length (L=longest axis) and width (W=shortest axis).

Tumor Volume (V) was calculated using formula: V=L× W2/2 (Unit: mm³), where L=length of tumor (mm) and w=width of tumor (mm). Mean tumor volume and % tumor growth inhibition (% TGI) were then calculated (SEM=standard error of mean).

Tumor Volume

|  | G1 | | G2 | | G3 | | G4 | |
| --- | --- | --- | --- | --- | --- | --- | --- | --- |
| Days | Mean | SEM | Mean | SEM | Mean | SEM | Mean | SEM |
| 1 | 147.56 | 20.68 | 145.40 | 29.19 | 146.92 | 19.97 | 146.87 | 23.57 |
| 6 | 331.93 | 79.52 | 174.90 | 37.07 | 198.50 | 31.03 | 146.27 | 38.93 |
| 9 | 463.77 | 110.07 | 261.95 | 66.94 | 363.14 | 70.22 | 179.96 | 59.99 |
| 13 | 617.07 | 146.04 | 340.62 | 93.64 | 463.30 | 111.28 | 252.51 | 90.77 |
| 16 | 961.26 | 226.49 | 448.05 | 121.72 | 709.65 | 163.77 | 295.39 | 110.81 |
| 20 | 1280.51 | 295.87 | 630.25 | 215.72 | 875.99 | 206.53 | 425.61 | 160.23 |

Tumor Growth Inhibition (%)

| Days | G1 | G2 | G3 | G4 |
| --- | --- | --- | --- | --- |
| 1 | 0 | 1.47 | 0.44 | 0.46 |
| 6 | 0 | 47.31 | 40.20 | 55.93 |
| 9 | 0 | 43.52 | 21.70 | 61.20 |
| 13 | 0 | 44.80 | 24.92 | 59.08 |
| 16 | 0 | 53.39 | 26.18 | 69.27 |
| 20 | 0 | 50.78 | 31.59 | 66.76 |

Bezafibrate by itself shows anti-tumor efficacy. It inhibits tumor formation by up to 40% on day 6. Bezafibrate in combination with sunitinib shows more than additive effect in inhibiting tumor growth. None of the treatment groups show any significant change in body weights.

Example 5: Pharmaceutical Compositions

Manufacturing formula for a pharmaceutical composition envisaged under the present invention can be referred herein below:

Capsules

| Ingredients | Formula I (mg) | Formula II (mg) | Formula III (mg) | Formula IV (mg) |
| --- | --- | --- | --- | --- |
| Bezafibrate | 100-400 | 100-400 | 100-400 | 100-400 |
| Cremophor ELP/RH 40 | 150-750 | 150-750 | 150-750 | 150-750 |
| Capmul MCM | 200-500 | 200-500 | 200-500 | 200-500 |
| Labrasol/transcutol HP/ethanol | — | 50-200 | — | — |
| Vitamin E TPGS | — | — | 10-50 | — |
| Gelucire 44/14 | — | — | — | 50-200 |

1) Cremophor/Gelucire was heated and melted.
2) Labrasol/transcutol/ethanol was added to the melt obtained in step (1).
3) Capmul MCM was added to the mixture obtained in step (2) to form a solution.
4) Vitamin E TPGS was heated and added dropwise to the solution obtained in step (3) and bezafibrate was added to this solution. (In examples which do not contain Vitamin E TPGS, only bezafibrate is added to the solution of step (3).
5) The solution obtained in step (4) was filled in soft or hard gelatin capsule.

Tablets

| Ingredients | Qty/Tab (mg) |
| --- | --- |
| Bezafibrate | 200-400 |
| Microcrystalline cellulose | 10-35 |
| Lactose | 50-200 |
| Croscarmellose Sodium | 2-10 |
| Povidone | 3-10 |
| Polysorbate 80 | 3-10 |
| Methylene chloride/water | q.s. |
| Hypromellose | 30-90 |
| Colloidal Anhydrous silica | 1-5 |
| Talc | 1-5 |
| Magnesium Stearate | 1-5 |
| Opadry ready mix | 10-20 |
| Purified water | qs |

1) Bezafibrate, microcrystalline cellulose, lactose and croscarmellose sodium were blended together to obtain a dry mix.
2) Polysorbate 80 was dissolved in half quantity of methylene chloride and water to obtain a solution.
3) Povidone was added in remaining quantity of methylene chloride and water and mixed and added to the Polysorbate 80 solution obtained in step (2) to form the binder solution.
4) The dry mix obtained in step (1) was granulated with the binder solution obtained in step (3) to obtain granules.
5) The granules obtained in step (4) were dried, sized and blended with hypromellose, colloidal anhydrous silica and talc.
6) The granules obtained in step (5) were lubricated with magnesium stearate and compressed into tablets and coated.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method for the treatment of renal cell carcinoma in a patient, the method comprising administering to said patient bezafibrate, or a pharmaceutically acceptable salt or prodrug thereof, in an amount effective to treat renal cell carcinoma.

2. The method according to claim 1, wherein the renal cell carcinoma comprises treat conventional (clear-cell) renal cell carcinoma, papillary renal cell-carcinoma, chromophobe renal carcinoma, onco-cytoma, or collecting-duct carcinoma.

3. The method according to claim 1, wherein the renal cell carcinoma comprises Stage I, Stage II, Stage III or Stage IV renal cell carcinoma.

4. The method according to claim 1, wherein bezafibrate is administered in combination with at least one other cancer therapy.

5. The method according to claim 4, wherein the additional cancer therapy comprises surgery, chemotherapy, immunotherapy, or ionizing radiation.

6. The method according to claim 5, wherein the additional cancer therapy comprises administering at least one additional agent comprising a nucleoside analogue, antifolate, antimetabolite, topoisomerase I inhibitor, anthracycline, podophyllotoxin, taxanes, vinca alkaloid, alkylating agent, platinum compound, proteasome inhibitor, nitrogen mustards, oestrogen analogue, monoclonal antibody, tyrosine kinase inhibitor, mTOR inhibitor, retinoid, immunomodulatory agent, histone deacetylase inhibitor, or other kinase inhibitor.

7. The method according to claim 6, wherein the at least one additional agent comprises bevacizumab, axitinib, sorafenib, sunitinib, everolimus, temsirolimus, pazopanib, or lenvatinib.

8. The method according to claim 6, wherein the at least one additional agent comprises sunitinib.

9. The method according to claim 6, wherein the at least one additional agent is administered simultaneously with bezafibrate.

10. The method according to claim 6, wherein the at least one additional agent is administered sequentially with bezafibrate.

11. The method according to claim 6, wherein the at least one additional agent is administered separately from bezafibrate.

12. The method according to claim 4, wherein the bezafibrate is administered prior to treatment with ionizing radiation.

13. The method according to claim 4, wherein the bezafibrate is administered subsequent to treatment with ionizing radiation.

14. The method according to claim 4, wherein the bezafibrate is administered prior to surgical treatment for renal cell carcinoma.

15. The method according to claim 4, wherein the bezafibrate is administered subsequent to surgical treatment for renal cell carcinoma.

* * * * *